(12) United States Patent
Sullivan et al.

(10) Patent No.: US 10,729,333 B2
(45) Date of Patent: Aug. 4, 2020

(54) SYSTEM AND METHOD FOR MONITORING PHYSIOLOGICAL ACTIVITY OF A SUBJECT

(71) Applicant: Sonomedical Pty Ltd, Balmian, New South Wales (AU)

(72) Inventors: Colin Edward Sullivan, Balmian (AU); Peter Charles Spencer, Balmian (AU); Mark Bradley Norman, Balmian (AU)

(73) Assignee: SONOMEDICAL PTY LTD, New South Wales (AU)

(*) Notice: Subject to any disclaimer, the term of this patent is extended or adjusted under 35 U.S.C. 154(b) by 218 days.

(21) Appl. No.: 15/106,794

(22) PCT Filed: Dec. 19, 2014

(86) PCT No.: PCT/AU2014/050440
§ 371 (c)(1),
(2) Date: Jun. 20, 2016

(87) PCT Pub. No.: WO2015/089591
PCT Pub. Date: Jun. 25, 2015

(65) Prior Publication Data
US 2017/0035303 A1    Feb. 9, 2017

(30) Foreign Application Priority Data

Dec. 20, 2013    (AU) .................... 2013905017

(51) Int. Cl.
*A61B 5/0205* (2006.01)
*A61B 5/113* (2006.01)
(Continued)

(52) U.S. Cl.
CPC ............ *A61B 5/0205* (2013.01); *A61B 5/024* (2013.01); *A61B 5/113* (2013.01); *A61B 5/4809* (2013.01);
(Continued)

(58) Field of Classification Search
CPC ..... A61B 5/0205; A61B 5/113; A61B 5/4809; A61B 5/6892; A61B 5/7221; A61L 35/4809
See application file for complete search history.

(56) References Cited

U.S. PATENT DOCUMENTS 5,479,932 A    1/1996  Higgins et al.
5,479,939 A    1/1996  Ogino
(Continued)

FOREIGN PATENT DOCUMENTS

JP    H04-053535 A    2/1992
JP    H04-272746 A    9/1992
(Continued)

OTHER PUBLICATIONS

Extended European Search Report from European Application No. 14871472.8, dated Apr. 25, 2017.
(Continued)

*Primary Examiner* — Michael R Bloch
(74) *Attorney, Agent, or Firm* — Morgan, Lewis & Bockius LLP

(57) ABSTRACT

A system and associated method is disclosed to monitor physiological activity of a subject. One or more sensors are positioned in or on a support, the support being adapted to receive the subject, at least a first one of the sensors being adapted to produce a first signal indicative of movement of the subject over time. Processing apparatus is adapted to identify first, second and third portions of the first signal. The first and third portions correspond to first and third time periods, respectively, during which the subject changes body position on the support. The second portion corresponds to a second time period, between the first and third time periods, during which substantially no change in body position of the subject on the support takes place.

15 Claims, 12 Drawing Sheets

(51) Int. Cl.
*A61B 5/00* (2006.01)
*A61B 5/024* (2006.01)

(52) U.S. Cl.
CPC .......... *A61B 5/4818* (2013.01); *A61B 5/6892* (2013.01); *A61B 5/7221* (2013.01); *A61B 5/7235* (2013.01); *A61B 2562/0204* (2013.01)

(56) References Cited

U.S. PATENT DOCUMENTS

| | | | |
|---|---|---|---|
| 2004/0111045 A1* | 6/2004 | Sullivan | A61B 5/11 600/595 |
| 2006/0064037 A1* | 3/2006 | Shalon | A61B 5/0006 600/586 |
| 2007/0232948 A1 | 10/2007 | Stadler et al. | |
| 2008/0275327 A1* | 11/2008 | Faarbaek | A61B 5/0002 600/382 |
| 2008/0312713 A1* | 12/2008 | Wilfley | A61B 5/053 607/41 |
| 2010/0030118 A1 | 2/2010 | Hiei et al. | |
| 2010/0152546 A1 | 6/2010 | Behan et al. | |
| 2010/0256512 A1* | 10/2010 | Sullivan | A61B 5/113 600/529 |
| 2011/0034811 A1* | 2/2011 | Naujokat | A61B 5/0245 600/484 |
| 2011/0046498 A1* | 2/2011 | Klap | A61B 5/0205 600/534 |
| 2011/0118614 A1* | 5/2011 | Brauers | A61B 5/02438 600/500 |
| 2012/0184825 A1 | 7/2012 | Ben David | |

FOREIGN PATENT DOCUMENTS

| | | |
|---|---|---|
| JP | 2007-175388 A | 7/2007 |
| JP | 2007-289660 A | 11/2007 |
| JP | 2008-142238 A | 6/2008 |
| WO | WO-2004/045407 | 6/2004 |
| WO | WO-2012/037614 | 3/2012 |

OTHER PUBLICATIONS

International Search Report and Written Opinion for Application No. PCT/AU2014/050440, dated Feb. 25, 2015, 15 pages.

Office Action issued in corresponding Japanese Patent Application No. 2016-559475, dated Oct. 15, 2018.

* cited by examiner

SYSTEM AND METHOD FOR MONITORING PHYSIOLOGICAL ACTIVITY OF A SUBJECT

CROSS-REFERENCE TO RELATED APPLICATIONS

The present application claims priority from Australian Provisional Patent Application No 2013905017 filed on 20 Dec. 2013, the content of which is incorporated herein by reference.

TECHNICAL FIELD

The present disclosure relates to a system for monitoring physiological activity of a subject, particularly, although not necessarily exclusively, using sensors located in or on a support against which the subject rests.

BACKGROUND

Many devices have been used and proposed for recording breathing or sleep activity. One example is an ECG measurement system in which ECG electrodes are attached to a subject's skin. Another example is an electronic stethoscope which is manually pressed against the subject to hold it in place against the subject's skin.

An alternative approach employs vibration sensors that are placed at different positions in a mat. The sensors are configured to sense vibrations from the patient, permitting diagnosis of breathing abnormalities, snoring and sleep apnea, etc. The sensors are distributed over the mat such that, when the subject rests against the mat, sensors may sense sound vibrations originating from the subject to enable a diagnosis to be performed.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

According to a first aspect, the present disclosure provides a system adapted to monitor physiological activity comprising:
one or more sensors positioned in or on a support, the support being adapted to receive a subject, at least a first one of the sensors being adapted to produce a first signal indicative of movement of the subject over time; and
processing apparatus adapted to:
receive the first signal from the first sensor;
identify a first portion of the first signal that corresponds to a first time period during which the subject changes body position on the support;
identify a third portion of the first signal that corresponds to a third time period during which the subject changes body position on the support; and
identify a second portion of the first signal that corresponds to a second time period, between the first and third time periods, during which substantially no change in body position of the subject on the support takes place.

In a second aspect, the present disclosure provides a method of monitoring physiological activity comprising:
identifying a first portion of a first signal, wherein the first signal produced by a first sensor positioned in or on a support adapted to receive a subject, the first signal being indicative of movement of the subject over a period of time, and wherein the first portion of the first signal corresponds to a first time period during which the subject changes body position on the support;
identifying a third portion of the first signal that corresponds to a third time period during which the subject changes body position on the support; and
identifying a second portion of the first signal, that corresponds to a second time period, between the first and third time periods, during which substantially no change in body position of the subject on the support takes place.

In a third aspect, the present disclosure provides software that, when installed on a computer, causes the computer to perform the method of the second aspect.

In a further aspect, the present disclosure provides a processor adapted to:
identify a first portion of a first signal, wherein the first signal is produced by a first sensor positioned in or on a support adapted to receive a subject, the first signal being indicative of movement of the subject over a period of time, and wherein the first portion of the first signal corresponds to a first time period during which the subject changes body position on the support;
identify a third portion of the first signal that corresponds to a third time period during which the subject changes body position on the support; and
identify a second portion of the first signal, that corresponds to a second time period, between the first and third time periods, during which substantially no change in body position of the subject on the support takes place.

Generally, the system, method, software and processor may monitor movement to identify, monitor and/or analyse a variety of different body parameters, behaviours and events, including, but not limited to, breathing, coughing, sneezing, heartbeat, heart rhythm disturbances, heart function, heart valve abnormalities and murmurs, body reflexes, body positioning, gut activity, jaw movements, snoring, sleep apnea, sleep state, restriction of airways, asthma, quiescent periods, period spent asleep or awake, fetal heart beat, fetal movements, placental blood flow, crackles, rhonchi, tales, indicia of lung infection, chronic lung disease and/or chronic heart failure.

The movement monitored by the one or more sensors may be vibrational movement. Thus, the one or more sensors may be vibration sensors and the first signal produced by the first vibration sensor may be indicative of vibrations caused by the subject over a period of time.

By positioning the one or more sensors in or on a support, rather than directly attaching sensors to the subject, the sensors are not necessarily in contact at all times with the subject and to this end can be considered "non-contact sensors". The subject may move freely in relation to the sensors and the sensors may be considered, in combination, to define a "sensor field".

The support may comprise a pad against which the subject rests, reclines or sits, for example. The pad may comprise foam or other cushioning material. The pad may be in the form of a mat or mattress, a seat cushion, back support or otherwise. The support may form part of a bed, trolley, cot, chair or other item against which the subject may sit or lie for a period of time.

The use of non-contact sensors in or on the support can provide a number of advantages. For example, the system may be safer and more user friendly for all subjects, including non-attended children being monitored at home. The subject may freely enter and leave the sensor field formed by a plurality of the sensors at the support. The subject may be considered a mobile, ambulatory, non-tethered subject in this regard. The system may be particularly suitable for monitoring of the subject while at rest, including when asleep or sedated (e.g., from anaesthetic). In this regard, the sensor field may be considered a localised sensor field at the place of rest of the subject. When used, for example, to assess sleep quality and quantity, the technique can have a minimal effect on sleep, particularly when conducted in the subject's home, e.g., in comparison to techniques that employ multiple attached sensors and leads. Further, the non-intrusive nature of non-contact sensors can facilitate better user acceptance and compliance, e.g., when used for long term monitoring purposes.

In one embodiment, where one or more vibrations sensors are used, the vibration sensors may comprise a vibration sensing element, e.g. a membrane, and the vibration sensors may produce an electrical signal based on movement of the membrane. In alternative embodiments, other types of sensors may be used. For example, ECG, EEG EOG and/or EMG sensors that are not attached to the subject may be used.

Since the one or more sensors are not directly attached to the subject, changes in position of a subject can have great effect on the quality of the signals produced by the sensors. Where vibration sensors are used, for example, vibrations caused by positional changes of the subject can substantially mask smaller vibrations, e.g., vibrations caused by breathing flow, which smaller vibrations may be of greater interest from a subject diagnosis perspective.

In general, references herein to "changes in body position of the subject" or similar are intended to describe gross body motion, which can involve changes in posture of the subject and/or changes in location of the subject on the support (e.g., as opposed to motion of a limited portion of the body such as chest movement during breathing). While in many instances changes in body position will therefore culminate in the subject having a different posture and/or location on the support, it should be recognised that in some instances a change in body position in the context of the present disclosure may culminate in the subject returning to the same posture and/or location on the support.

The identification of portions of the first signal that correspond to periods of body position movements and periods between body position movements, e.g., periods of rest, can enable a number of advantages to be realised. For example, analysis of smaller movements, e.g. smaller vibrations, such as breathing flow vibrations and heart sound vibrations, can be carried out with greater accuracy by considering the signal at periods of rest only. Further, the efficiency of the analysis may be increased by selecting more relevant portions of the signal for analysis only. Still further, the identification of periods of rest (also termed quiescent or quiescence periods) and periods of body position movement, can be used as part of a particular diagnosis, e.g., if sleep state etc., is being assessed. Additional advantages will also become apparent from the subsequent discussions.

Where one or more vibration sensors are used, the vibration signal may be an acoustic (sound) signal and the one or more vibration sensors may be acoustic sensors. Nonetheless vibration signals with frequencies outside of the range of hearing may also be used.

In this discussion, for simplicity, reference is made to first, second and third portions of the signal that correspond, respectively, to a first time period during which the subject changes body position on the support, a subsequent second time period during which the subject makes substantially no change in body position on the support, and further subsequent third time period during which the subject again changes body position on the support. However, the system and method is not necessarily limited to identifying three portions of the signal only. Indeed, over the course of a phase of monitoring, multiple portions of the signal that correspond to time periods during which the subject changes body position on the support may be identified (i.e. multiple first and/or third portions of the signal may be identified), along with multiple intermediate time periods during which the subject makes substantially no change in body position (i.e. multiple second portions of the signal may be identified). Thus, a third portion of the signal, immediately following a period in which the subject makes substantially no change in body position on the support, may also be considered to provide a first portion of the signal immediately preceding the next period in which the subject makes substantially no change in body position on the support. This process can be described as a moving window of sampling that can be carried out over a long recording period (e.g., over multiple hours of recording).

One or more of the first, second and third portions of the first signal, from the first sensor, may be identified by analysis of parameters of the signal, such as the amplitude, duration, frequency content, and timbre. For example, the amplitude of a vibration signal may be relatively high during periods of body movement and relatively low during periods of rest. The amplitude of the vibration signal may therefore be compared with one or more predetermined threshold amplitudes to determine if the vibration signal, at any point in time, is indicative of a change in body position of the subject on the support or a period of rest.

Additionally or alternatively, one or more of the first, second and third portions of the first signal, from the first sensor, may be identified based on analysis of a different signal, generated from a different sensor. The different signal/sensor may be the same or an alternative type of signal/sensor to the first signal/sensor. As an example, one or more vibration sensors and one or more displacement sensors may be provided in or on the support. First, second and third portions of a first vibration signal, from a first vibration sensor, may be identified based on analysis of one or more displacement signals from the one or more displacement sensors. The displacement sensors may comprise a PVDF coaxial cable, for example, that extends across the support. The displacement sensors may each generate a displacement signal indicative of periods of changes in body position and periods of rest. By time-matching the vibration signal with a displacement signal, one or more of the first, second and third portions of the vibration signal can be identified based on an analysis of the displacement signal.

After identification of the first, second and third portions of the signal, any one or more of the first, second and third portions of the signal may be subjected to further analysis. In one embodiment, the second portion of the signal, which corresponds substantially to a period of rest, may be subjected to further analysis.

As an initial step or otherwise, the second portion of the signal may be analysed to determine if it is of sufficient quality to provide useful information for diagnostic purposes, i.e. it is of sufficient quality to be a signal of interest.

Determining whether or not the second portion of the signal is of sufficient quality may be achieved by determining if the amplitude of the signal, e.g. at one or more particular frequencies, exceeds a predetermined threshold level. However, care must be taken, particularly where analysis of breathing quality or sleep apnea, etc., is being carried out, not to rule out the possibility that a lower amplitude of the signal is a direct result of breathing difficulties or sleep apnea, etc. In these circumstances, signal amplitudes at frequencies related to breathing function may be low but the quality of the signal may in fact be high. Similar care must be taken where a pathology exists that causes intermittent vibrations, such as wheezing, crepitations (lung crackles), snoring, teeth grinding, heart murmurs, or abnormal breathing patterns, which may in turn cause absence of a strong signal for a substantial period of time, even when the quality of the signal is high.

In consideration of this problem, in one embodiment, the system is adapted to identify a feature of the second portion of the signal that corresponds to a heartbeat of the subject, and determine if that feature of the signal is above or below a predetermined signal threshold. On the assumption that the subject's heart is beating properly, the amplitude of the heartbeat feature of the signal can be indicative of the proximity of the subject's heart to the sensor. Since the heart position is relatively fixed in relationship to the thorax of the subject, the amplitude of the heartbeat feature of the signal has been found to be a particularly effective parameter for determining signal quality where breathing related conditions are under analysis. Thus the heartbeat feature of the signal may be used as a continuing reference signal to which other features of interest of the signal (e.g. breathing flow sounds) are compared.

An additional or alternative approach to determining whether or not the second portion of the signal is of sufficient quality to be a signal of interest involves evaluating a part of, or the entire period of, the second portion. Typically, if the signal is of a sufficient quality for any part of the second portion then this indicates that the signal quality will be sufficient for the entire period of the second portion. This is because there is substantially no change in body position of the subject during the second portion and the proximity of the subject to the sensor during the second portion therefore remains substantially constant. Further, during the second portion, there are no large interfering signals such as those from body position changes to mask the lower magnitude signals of interest. When, for example, a breathing signal is identified during only part of the second portion, the part of the second portion where no breathing signal is identifiable is highly indicative of sleep apnea. Likewise if breath sounds including wheeze are detected during a first part of the second portion, but breath sounds with no wheeze are detected for a latter part of the second portion, it is highly indicative that the subject is not wheezing during the latter part of the second portion, rather than it being indicative that the signal is of lower quality at this point in time.

An additional or alternative approach to determining whether or not the second portion of the first signal from the first sensor is of sufficient quality to be a signal of interest involves comparing the second portion of the first signal from the first sensor with a corresponding portion of a signal generated from another sensor and determining relative signal quality of the two second portions. This approach may be carried out as part of an optimisation procedure.

In more detail, in addition to the first sensor, at least a second sensor positioned in or on the support can be provided, the second sensor adapted to produce a second signal indicative of movement of the subject over a period of time. The processor of the system may be adapted, and/or the method may comprise steps, to:

receive the second signal from the second sensor;
  identify a first portion of the second signal that corresponds to the first time period, during which the subject changes body position on the support;
  identify a third portion of the second signal that corresponds to the third time period, during which the subject changes position on the support;
  identify a second portion of the second signal, that corresponds to the second time period, between the first and third time periods, during which substantially no change in body position of the subject on the support takes place; and
  compare at least part of the second portion of the second signal with a corresponding part of the second portion of the first signal.

The provision of a plurality of sensors to detect movement, e.g. a plurality of vibration sensors or otherwise, which sensors can be provided at different parts of the support, can reduce difficulties with obtaining a high quality signal when a subject changes body position on the support. Since the sensors are not affixed to the subject, as the subject moves on the support away from one of the sensors, the strength/quality of the signal from that sensor is likely to reduce. However, the subject may nevertheless move towards another of the sensors (or at least move less far away from that other sensor), such that at least one of the sensors provides a signal of sufficient quality for diagnostic purposes. At any point in time, more than one of the sensors may provide a signal of sufficient quality or only one sensor may provide a signal of sufficient quality. Regardless, when multiple sensors are provided, and thus multiple signals are produced, the highest quality signal can be selected at any point in time and/or for any time period, as part of an optimisation procedure.

One advantage of identifying the first, second and third portions of the signals is that these signal portions correspond to time periods in which it is predictable that the quality of the signals will change or remain constant. Generally, during the second time period, the subject remains substantially at rest on the support. Therefore, the quality of the second portion of the signal from each sensor, and the relative quality of the second portion of the signal between different sensors, is likely to remain substantially the same across the entire second time period. However, when a subject moves during both the first and third time periods, the quality of the portions of the signal corresponding to those periods is likely to be in a state of change. The first and third time periods are periods of transition for each sensor, with the quality of the signal from the sensor immediately after the first or third time period being likely to have changed in comparison to the quality of that signal from that sensor immediately before that first or third time period. Furthermore, the quality of the signal from one of the sensors immediately after the first or third time period is likely to have changed in comparison to the quality of the signal from another of the sensors immediately after the corresponding time period.

Determining when the quality of a signal is likely to have changed can be particularly beneficial if 'real-time' analysis of the signals is performed, for example. While in some embodiments, a contiguous record of the signals indicative of movement for a subject over an extended period of time can be generated and recorded, and analysis of the signals performed subsequently, e.g., after the subject removes themselves from the support, in other embodiments, analysis may be performed in real-time. Real-time analysis may be particularly useful if an immediate warning of breathing or other difficulties is required. The system may provide an audible and/or visual alert signal when breathing difficulties have been detected (e.g. a period of apnea or wheezing) or periods of heart abnormalities (e.g. arrhythmias, etc.). Regardless of the reasons for real-time monitoring, it may not be desirable to continually compare the quality of signals from multiple sensors as part of an optimisation process. For example, continuous comparisons may be a drain on processing power and may increase the risk of errors in the system. By identifying portions of the signals from the sensors that correspond to time periods during which the subject changes body position on the support, comparisons of the quality of signals from different sensors may be carried out more selectively. For example, comparisons of signal quality between different sensors may be carried out shortly after a period of change of body position, e.g. within a 30 second, 20 second or 10 second period after the end of the first period or third period or from the start of the next period.

Following from the discussions above, according to one aspect, the present disclosure provides a system for monitoring physiological activity comprising:

at least first and second sensors positioned in or on a support, the support being adapted to receive a subject, each of the first and second sensors adapted to produce a first and second signal, respectively, indicative of movement of the subject over a period of time;

processing apparatus adapted to:

receive the first and second signals from the first and second sensors;

identify a first portion of each of the first and second signals that corresponds to a first time period during which the subject changes body position on the support;

identify a second portion of each of the first and second signals that corresponds to a second time period, that immediately follows the first time period, during which substantially no change in body position of the subject on the support takes place; and compare the signal quality substantially at the start at least of the second portion of the first signal with the signal quality substantially at the start at least of the second portion of the second signal, and select the second portion of the first or second signal with higher signal quality for further analysis.

Additional sensors may be provided. For example, in one embodiment, first, second, third and fourth sensors are positioned in or on the support, the first, second, third and fourth sensors adapted to produce first, second, third and fourth signals, respectively, indicative of movement of the subject over a period of time, and the processing apparatus is adapted to:

receive the first, second, third and fourth signals from the first, second, third and fourth sensors;

identify a first portion of each of the first, second, third and fourth signals that corresponds to a first time period during which the subject changes body position on the support;

identify a second portion of each of the first, second, third and fourth signals that corresponds to a second time period, that immediately follows the first time period, during which substantially no change in body position of the subject on the support takes place; and compare the signal quality substantially at the start at least of the second portion of every one of the first, second, third and fourth signals, and select the second portion of the first, second, third or fourth signal with higher signal quality for further analysis.

In any of the aspects disclosed, the signal from one or more of the vibration sensors may be split into separate channels. The signal may be split into separate channels according to frequency or otherwise. The analysis and comparison techniques described above can be carried out on the entire signal and/or separate channels of the signal.

Particularly where analysis of breathing is performed and vibration sensors are employed, for example, the vibration signals may each be split into a first signal based on breathing effort or breathing movement frequency (hereinafter a breathing effort signal) and a second signal based on breathing flow frequency (hereinafter a breathing flow signal). Breathing effort is linked to movement of the subject's diaphragm and therefore has a relatively low frequency with relatively high amplitude. On the other hand, breathing flow frequencies tend to be of much higher frequency, generated through high frequency vibration of membranes or obstructions in the body, etc., but of relatively low amplitude. By splitting the vibration signal into separate signals, more targeted analysis of the vibration signal may be performed, e.g., depending on whether or not breathing effort, breathing flow or a combination of breathing effort and breathing flow is to be analysed, in order to arrive at a diagnosis.

Analysis of the quality of the various portions of the vibration signal may be carried out on each of the breathing effort and breathing flow signals separately or in combination. It is recognised, for example, that the relative quality of one of these signals may be different to the other, for any given vibration signal from a vibration sensor. To this end, during the optimisation process, for the same time period, a breathing effort signal from one sensor may be selected as optimal in combination with a breathing flow signal from a different sensor.

As indicated, one or more of the identified first, second and third portions of the signal obtained from one of the sensors may be subjected to further analysis, e.g. once the quality of the signal has been assessed and/or an optimal signal has been selected or assembled. Analysis of the second portion, which corresponds to a period of rest, may be carried out, for example.

Through analysis of selected portions of the signal, the system and method may be used to detect movements that can allow diagnosis of central sleep apnea, obstructive sleep apnea or mixed sleep apnea. In general, apneic events are characterised by pauses in or obstructions to breathing. In the present disclosure, the pauses or obstructions can be identified through analysis of the breathing effort signal and/or the breathing flow signal.

Central apnea occurs when no direction to breathe is transmitted from the brain. Central apnea can therefore be determined through identification of a pause in both the breathing effort signal and the breathing flow signal. The pause may be identified as a period in which the signal level does not rise above background noise for a period, of time exceeding a threshold period of time, the pause being immediately preceded and followed by periods in which the signal level does rise above background noise. Additionally or alternatively, the pause may be identified as a period in which the signal level has a reduction in amplitude, e.g. of at least 90%, in comparison to preceding and/or subsequent periods, for a period of time exceeding a threshold period of time. The threshold period of time may be 10 seconds for adults or equivalent to 2 breathing cycles for children, for example.

Obstructive apnea occurs upon obstruction of the upper airway, e.g. when relaxation causes the palate and tongue to close the upper airway (throat). Obstructive apnea can therefore be determined through identification of a pause in the breathing flow signal but not the breathing effort signal. Such events have continued breathing efforts but reduced or absent breathing airflow. Again, the pause may correspond to a period in which the signal level does not rise above background noise or corresponds to a reduction in amplitude, e.g. of 90%, in comparison to preceding and/or subsequent time periods, for a period of time exceeding the threshold period.

Mixed apnea occurs when, over a predetermined analysis period, both central apnea and obstructive apnea can be identified. Mixed apnea can therefore be determined based on a combination of the approaches taken to determining central and obstructive apnea.

Through analysis of selected portions of the signals, the system and method may be used for diagnosis of other events or conditions such as short cycle apneic events, breathing pattern changes such as Cheyne-Stokes breathing, hypopneic breathing, non-apneic, non-hypopneic partially obstructed breathing (simple snoring), REM related heartbeat patterns, wheezing, lung crackles (crepitations), leg movements, abnormal body movements, teeth grinding and jaw movements, lung infection, heart murmurs, heart rhythm abnormalities, and fetal movements.

Another advantage of identifying the first, second and third portions of the signals is that they can enable identification and quantification of periods of sleep, periods of intention to sleep, or periods of wakefulness, etc.

According to one aspect, the present disclosure provides a system adapted to estimate duration of a period of sleep of a subject comprising:
  one or more sensors positioned in or on a support, the support being adapted to receive a subject, at least a first one of sensors being adapted to produce a signal indicative of activity of the subject over time including the subject changing body position and respiratory events of the subject; and
    processing apparatus adapted to:
    identify a first portion of the signal that corresponds to a first time period during which the subject changes body position on the support;
    identify a third portion of the signal that corresponds to a third time period during which the subject changes body position on the support;
    identify a second portion of the signal, that corresponds to a second time period, immediately between the first and third time periods, during which substantially no change in body position of the subject takes place;
    identify one or more respiratory indicators of sleep in the second portion of the signal;
    estimate sleep onset time of the subject as the earlier of:
      (i) a predetermined threshold time (x), if the second period of time extends after the end of the first period of time for a time that is equal to or greater than the predetermined threshold time (x); or
      (ii) a time at which the earliest respiratory indicator of sleep in the second portion of the signal is identified; and
    calculate a duration of a period of sleep of the subject as the time between the estimated sleep onset time and the start of the third time period.

According to another aspect, the present disclosure provides a method of estimating duration of a period of sleep of a subject comprising:
  identifying a first portion of a signal, wherein the signal is produced by a sensor positioned in or on a support adapted to receive a subject, the signal being indicative of activity of the subject over a period of time including the subject changing body position and respiratory events of the subject, and wherein the first portion of the signal corresponds to a first time period during which the subject changes body position on the support;
  identifying a third portion of the signal that corresponds to a third time period during which the subject changes body position on the support;
  identifying a second portion of the signal, that corresponds to a second time period, immediately between the first and third time periods, during which substantially no change in body position of the subject takes place;
  identifying one or more respiratory indicators of sleep in the second portion of the signal; and
  estimating sleep onset time of the subject as the earlier of:
    (i) a predetermined threshold time (x), if the second period of time extends after the end of the first period of time for a time that is equal to or greater than the predetermined threshold time (x); or
    (ii) a time at which the earliest respiratory indicator of sleep in the second portion of the signal is identified; and
  calculating a duration of a period of sleep of the subject as the time between the estimated sleep onset time and the start of the third time period.

In general, if a subject lies immobile for a long period they are more likely to be asleep than if they are immobile for only short periods of time. The entirety of such a period of quiescence (a period where substantially no change in body position of the subject takes place) is not necessarily associated with sleep. However, sleep can be estimated to have occurred after a predetermined threshold time from the start of quiescence has elapsed, based on probability analysis.

Calculating a duration of sleep of a subject based only on periods of quiescence and body movement can be problematic, however in the presence of sleep disordered breathing (SDB). Snoring and respiratory events can disrupt sleep resulting in very short periods of sleep and, potentially, very short periods of quiescence. If SDB is present, and only gross body movements and periods of quiescence are used in the estimation of sleep, short periods of quiescence may be incorrectly classified as wake. Nonetheless, the presence of respiratory indicators of sleep can be used to increase probability of sleep being present to 100%, regardless of quiescence duration. Following from this, the present disclosure estimates of a sleep onset time if a subject is quiescent for >x seconds or a respiratory indicator of sleep is present in the period ≤x seconds. The approach permits the inclusion of very short periods of quiescence as sleep and allows for a more robust method of identifying sleep onset and sleep duration.

Again, the one or more sensors positioned in or on a support may be vibration sensors adapted to produce a signal indicative of vibration caused by the subject over time. However, alternative types of sensors may be used, such as ECG, EEG, EMG and EOG sensors.

Respiratory indicators of sleep may include snoring and/or breath sound changes, for example.

In the above aspects, changes in body position of the subject, and respiratory events, are assessed using sensors such as vibration sensors located in or on a support for receiving the subject. In alternative embodiments, other types of sensors, such as microphones, may be employed to assess one or both of these parameters, and which other sensors may or may not be positioned in or on any support for receiving the subject.

Thus, according to one aspect, the present disclosure provides a system adapted to estimate duration of a period of sleep of a subject comprising:

one or more sensors adapted to monitor changes in body position of the subject and respiratory indicators of sleep from the subject; and processing apparatus adapted to:
identify a quiescence time period during which substantially no change in body position of the subject takes place, the time period starting immediately after the end of a first body movement and ending immediately before the Start of a second body movement;
identify one or more respiratory indicators of sleep from the subject during the quiescence time period;
estimate sleep onset time of the subject as the earlier of:
(i) a predetermined threshold time (x), if the quiescence time period extends time that is equal to or greater than the predetermined threshold time (x); or
(ii) a time at which the earliest respiratory indicator of sleep during the quiescence time period is identified; and
calculate a duration of a period of sleep of the subject as the time between the estimated sleep onset time and the start of the second body movement.

Further, according to another aspect, the present disclosure provides a method of estimating duration of a period of sleep of a subject comprising:

identifying a quiescence time period during which substantially no change in body position of a subject takes place, the time period starting immediately after the end of a first body movement of the subject and ending immediately before the start of a second body movement of the subject;

identifying one or more respiratory indicators of sleep from the subject during the quiescence time period;
estimating sleep onset time of the subject as the earlier
(i) a predetermined threshold time (x), if the quiescence time period extends for a time that is equal to or greater than the predetermined threshold time (x); or
(ii) a time at which the earliest respiratory indicator of sleep during the quiescence time period is identified; and
calculating a duration of a period of sleep of the subject as the time between the estimated sleep onset time and the start of the second body movement.

In these aspects, substantially no change in body position of the subject may be considered to have taken place if any body movement that is identifiable lasts less than a body movement threshold time (y). The threshold time (y) can be determined as a time period where, when movement lasts for a time less than that time period (y), the subject has a very high probability of remaining in a sleep state. Following from this, the first and third time periods identified in preceding aspects exceed the body movement threshold time (y).

In one embodiment, the predetermined threshold time (x) in any of the preceding aspects is chosen to reflect a 90%, 95% or 99% probability that sleep onset has occurred, for example. In one embodiment, x is between 90 and 130 seconds, e.g., about 110 seconds, and y is between about 10 and 20 seconds, e.g., about 16 seconds. In practice, however, values for x and y will change for subjects falling in different age groups, with different pathologies, and different genders, and for subjects being monitored in different locations (e.g., when sleeping at home, or when sleeping in a hospital or laboratory), etc.

In the above aspects or otherwise, an "intention to sleep" time may be estimated. This may be take advantage of the fact that the sensors are provided in or on a support, e.g. as opposed to being directly attached to the subject, and therefore moveable with the subject when they move away from the support. Thus, to the extent that the sensors can recognise that a subject has been received by the support (e.g. is lying on or against the support), onset of an intention to sleep can be readily calculated. An intention to sleep time can be estimated as the total time that the subject is sensed on the support, e.g. through sensing movement, vibrations, heart beat and/or breathing, sounds, etc. In some embodiments, the intention to sleep time can be estimated as the total time that the subject is sensed on the support up to the time at which sleep onset is estimated to have started.

The approach may prevent overestimates of intention to sleep time since it can more accurately identify onset of an intention to sleep, e.g. in comparison to a system which relies on mere activation of apparatus, at which point the subject may have no intention to sleep.

Related to this, it can be seen that the systems and methods of the present disclosure can provide a means of surveillance of the subject. In contrast to a monitoring system that relies on tethering of sensors to the subject, the systems and methods, which use non-contact sensors, can permit a more holistic monitoring of the subject to take place. Not only can smaller movements such as breathing movements of the subject be monitored, but the location and movement of the mobile, ambulatory, non-tethered subject relative to a support can also be monitored. Where the support is a bed, for example, the sensors can be used to determine if the patient is on the bed, off the bed, and/or moving on the bed, for example.

Generally, it will be recognised that a processor or processing apparatus as disclosed herein may comprise a number of control or processing modules for controlling one or more components of the apparatus and may also include one or more storage elements, for storing vibration signal data, analysis data, and patient data, etc. The modules and storage elements can be implemented using one or more processing devices and one or more data storage units, which modules and/or storage devices may be at one location or distributed across multiple locations and interconnected by one or more communication links. Processing devices may include computers, tablets, smartphones, personal digital assistants and other types of computing devices, including computer systems manufacture specifically for the purpose of carrying out methods according to the present disclosure.

The processing modules can be implemented by a computer program or program code comprising program instructions. The computer program instructions can include source code, object code, machine code or any other stored data that is operable to cause the processor or processing apparatus to perform the steps described. The computer program can be written in any form of programming language, including compiled or interpreted languages and can be deployed in any form, including as a stand-alone program or as a module, component, subroutine or other unit suitable for use in a computing environment. The data storage device(s) may include suitable computer readable media such as volatile (e.g. RAM) and/or non-volatile (e.g. ROM, disk) memory or otherwise.

Signal analysis carried out in accordance with the present disclosure, e.g., to identify portions or features of signals corresponding to changes in body position breathing-related events, heartbeats or otherwise, may employ a variety of different signal processing techniques. Amplitude analysis, time domain analysis and/or frequency domain analysis may be carried out, utilising RMS values, variance, probability density, time history, impulse response, correlation, covariance, filters and/or Fourier transforms, for example.

BRIEF DESCRIPTION OF DRAWINGS

FIG. 6a shows another example of an image produced by a display device of the apparatus of FIG. 1, and FIGS. 6b and 6c show different composite signals derived from signals represented in the image of FIG. 6a;

DESCRIPTION OF EMBODIMENTS

Figure 1:
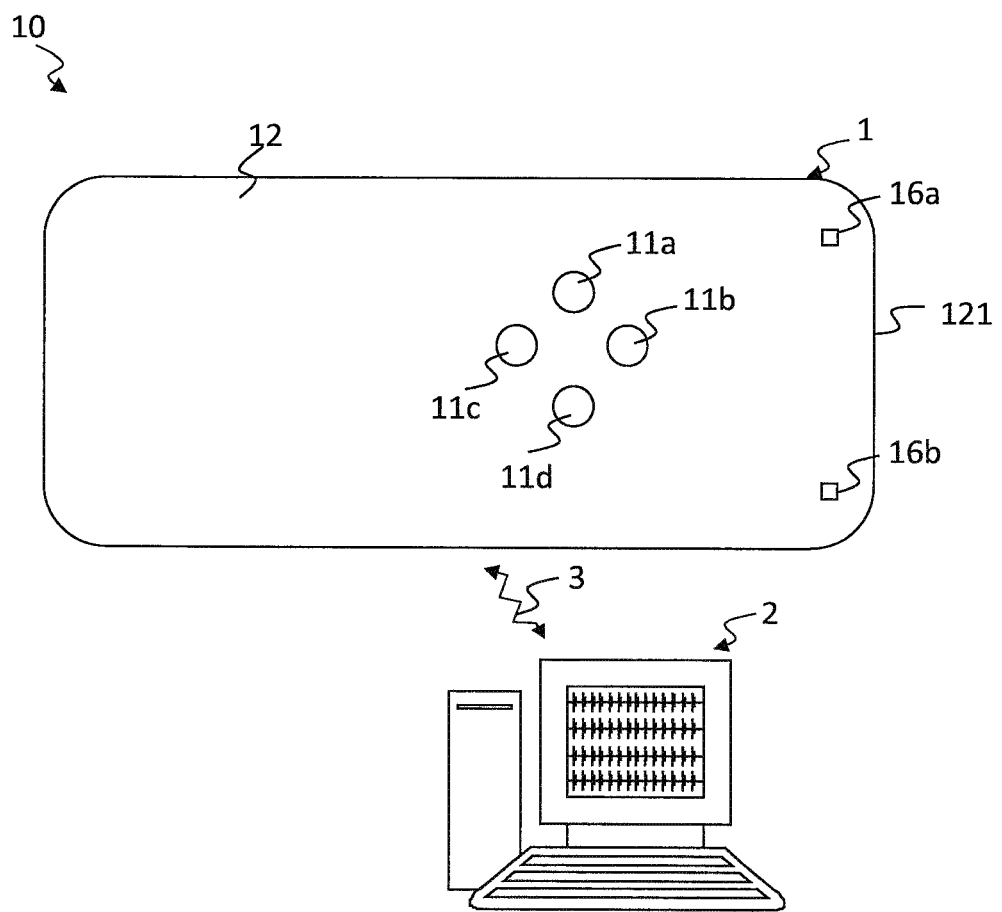
FIG. 1 shows a schematic illustration of physiological activity monitoring apparatus according to an embodiment of the present disclosure.

Physiological activity monitoring apparatus 10 of a system according to an embodiment of the present disclosure is illustrated in FIG. 1. The apparatus 10 includes a support, in particular a mattress 1, adapted to receive a subject in a recumbent position, and a workstation 2. The mattress 1 includes foam and a plurality of vibration sensors 11a-d, in particular a first vibration sensor 11a, a second vibration sensor 11b, a third vibration sensor 11c and a fourth vibration sensor 11d, positioned within respective recesses in the foam. A top surface of the vibration sensors 11a-d is located substantially flush with or projecting from a top surface 12 of the mattress 1 such that any one or more of the sensors 11a-d may press against the recumbent subject at any point in time. Nonetheless, a sheet or other covering may be positioned over the sensors 11a-d and/or mattress 1, between the vibration sensors 11a-d and the subject. The vibration sensors 11a-d are located at a position that is roughly one third of the length of the mattress 1 from a head end 121 of the mattress 1. This position is intended to correspond to a position at which the subject's chest is located. The vibration sensors 11a-d are "non-contact sensors" since they are not affixed to the subject. The subject may therefore move freely in relation to the sensors 11a-d. In this embodiment, the four vibration sensors 11a-d are distributed in an array configuration, in particular a diamond configuration. While vibration sensors are described in this detailed description, other types of sensors may be used as an alternative or in addition to vibration sensors. For example EEG, ECG, EMG or EOG sensors may be used. The apparatus may further include one or more microphones 16a, 16b as shown in FIG. 1, which may be used in conjunction with the vibration sensors to sense activity of the subject.

Figure 2:
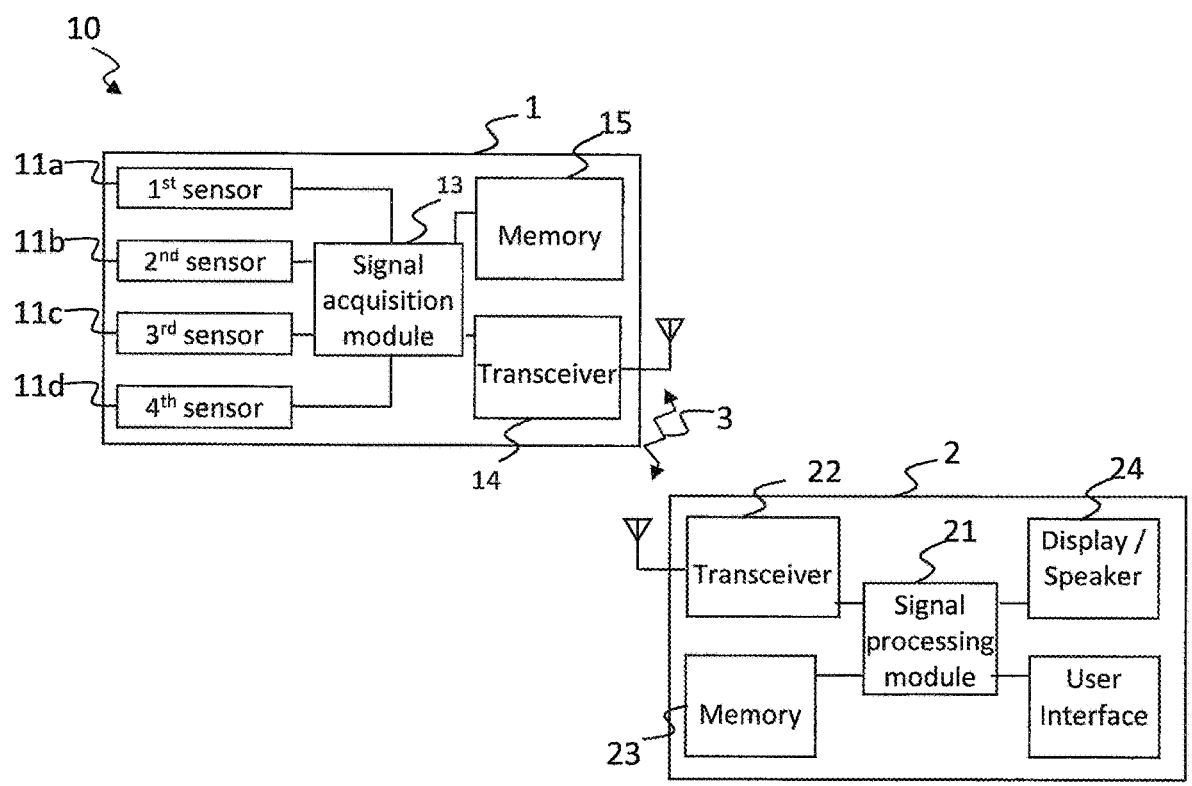
FIG. 2 shows a schematic illustration of components of the apparatus of FIG. 1.

Referring to FIG. 2, the monitoring apparatus 10 comprises processing apparatus including a signal acquisition module 13 located in or adjacent the mattress 1, and a signal processing module 21 provided in the workstation 2. When a subject lies on the mattress 1, each of the first to fourth vibration sensors 11a-d is adapted to produce a corresponding vibration signal indicative of sensed vibrations from the subject over a period of time.

The vibration signals are acquired by the signal acquisition module 13 and signal data is optionally stored in a memory 15. The vibration signals are then transmitted from the mattress 1 by a transceiver 14, over a wireless communication link 3, to the workstation 2. The signals are received at the workstation 2 by a further transceiver 22 and are subjected to processing by the signal processing module 21. The received signals can be stored in a further memory 23. In alternative embodiments, a wired communications link may be used in place of the wireless link 3.

The signal processing module 21 in this embodiment is adapted to cause images to be displayed on the display device 24 of the workstation 2, which images provide graphical representations of the vibration signals. An example of such an image 4a is provided in FIG. 3.

The signal processing module 21 is configured to split each of the first to fourth vibration signals into separate channels on a frequency-specific basis. In particular, the signal processing module splits each of first to fourth vibration signals, produced by the first to fourth vibration sensors 11a-d, respectively, into a breathing effort signal and a breathing flow signal. Breathing effort is linked to movement of the subject's diaphragm and therefore has a relatively low frequency but relatively high gain. On the other hand, breathing flow frequencies are much higher but of relatively lower gain, and are generated by vibrations caused by turbulence of air flow through the upper airways and in the lung airways, or by obstructions in the body, etc. By splitting the vibration signals in this manner (with both amplitude and frequency), a targeted analysis of each of these signal types can be performed by the signal processing module. For each sensor 11a-d, the breathing effort signal and the breathing flow signal are represented separately in the images, and marked in FIG. 3 with reference numbers 41a-d and 42a-d, respectively.

Figure 4:
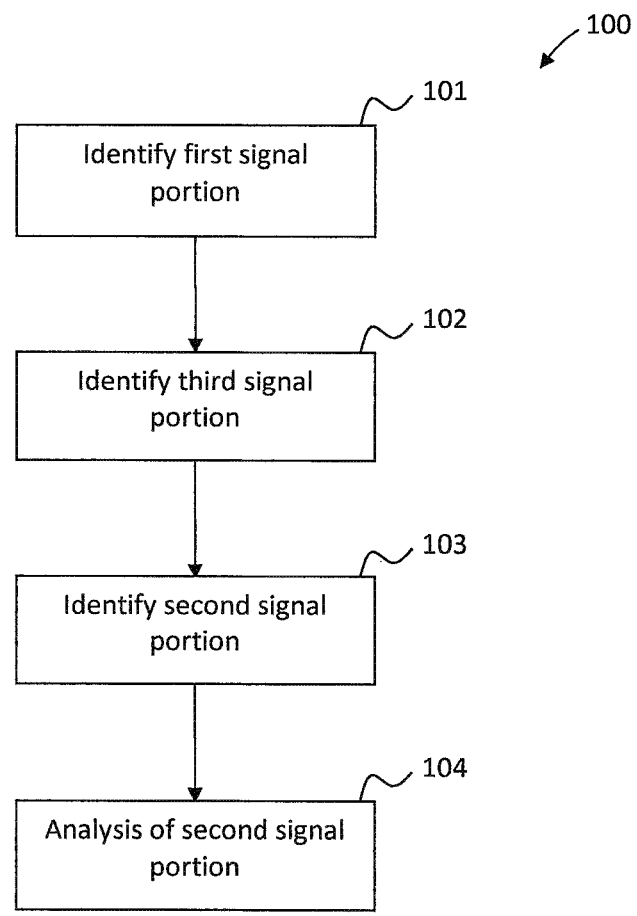
FIG. 4 shows a flowchart that represents steps carried out by processing modules of the apparatus of FIG. 1.

In this embodiment, with reference to flowchart 100 of FIG. 4, at 101 the signal processing module is adapted to, for both the breathing effort signal and the breathing flow signal from each of the first to fourth sensors 11a-d, identify a first portion of the signal that corresponds to a first time period during which the subject changes body position on the mattress 1. At 102, the processing module is also adapted to identify a third portion of that signal that corresponds to a third time period during which the subject changes body position on the mattress 1. At 103, the processing module is adapted to identify a second portion of the first signal that corresponds to a second time period, between the first and third time periods, during which substantially no change in body position of the subject on the mattress 1 takes place. At 104, the processing module subjects any one or more of the first, second and third portions of the signal, e.g. the second portion, to further analysis.

Figure 3:
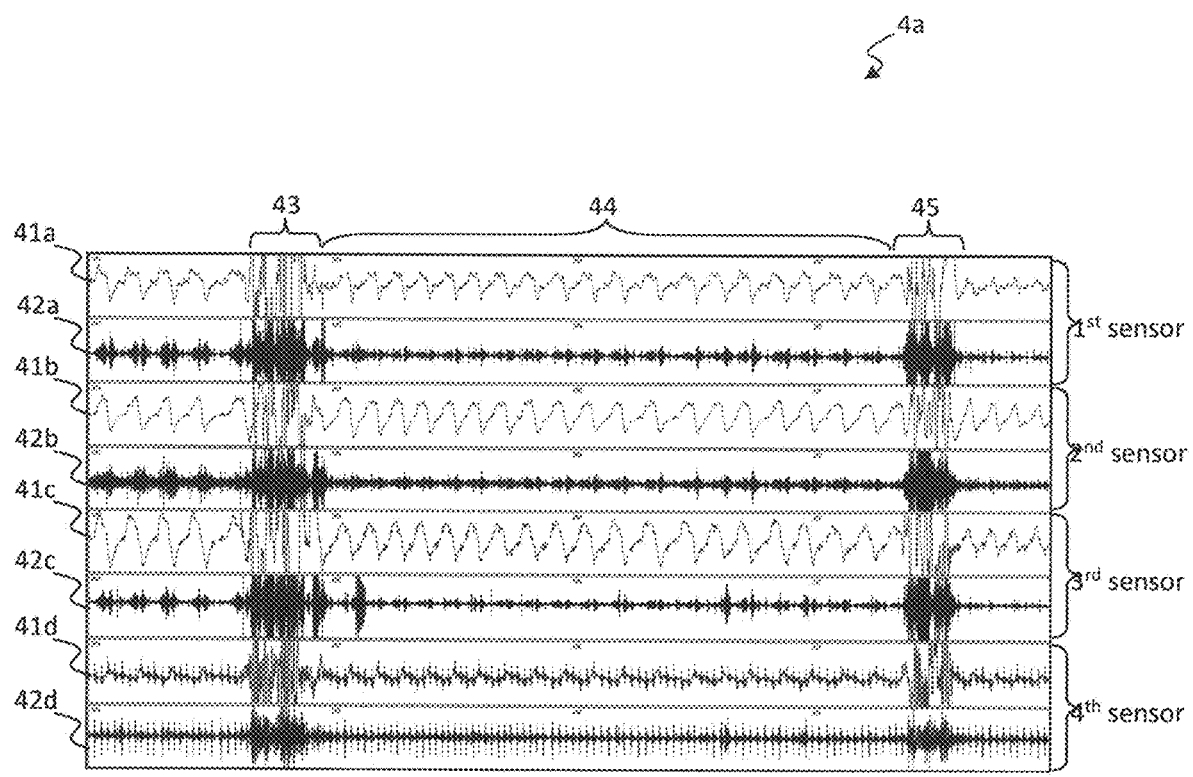
FIG. 3 shows an example of an image produced by a display device of the apparatus of FIG. 1.

The signal processing module 21 is adapted to identify the first and third portions of the vibration signal by comparing the amplitude of the vibration signal with a predetermined threshold amplitude. In FIG. 3, for each signal 41*a-d*, 42*a-d* from each sensor 11*a-d*, a relatively large signal amplitude exceeding the predetermined threshold amplitude is evident during two time periods. The portions of each vibration signal corresponding to these two time periods are identified in FIG. 3 as first portion 43 and third portion 45. As indicated, these portions 43, 45 correspond to time periods in which the subject has changed body position (i.e. periods of gross body movement of the subject). Based on identification of the first and third portions 43, 45 or otherwise, the signal processing module is also adapted to identify a second portion 44 of each vibration signal, which falls directly between the first and third portions 43, 45, and which corresponds to a period in which there is substantially no change in body position of the subject.

Since the sensors 11*a-d* are not directly attached to the subject, movement of the subject can have a considerable effect on the nature of the vibrations sensed by the sensors 11*a-d*. Vibrations caused by positional changes of the subject substantially mask smaller vibrations caused by breathing effort and breathing flow. In FIG. 3, the small vibrations caused by breathing effort and breathing flow are readily evident in the second portion 44 of each of the signals, but not in the first and third portions 43, 45 of the signals.

While FIG. 3 illustrates two portions 43, 45 of each signal that correspond to positional changes of the subject, over a longer period of time, e.g., during a night's sleep, there can be many more positional changes of the subject. Following from this, over the course of a phase of monitoring, the signal processing module 21 is adapted to identify multiple portions of the vibration signal that correspond to time periods during which the subject changes body position, along with multiple intermediate time periods during which the subject makes substantially no change in body position.

By identifying time periods during which the subject makes substantially no change in body position, the signal processing module can in one embodiment perform a targeted analysis of breathing, effort and breathing flow vibrations during these periods only.

Additionally or alternatively, by identifying periods of rest, in addition to periods of body position movement, the signal processing module can in one embodiment make detailed assessments of sleep state. Further, certain patterns of body position movement may be identified, for example, and the patterns may be correlated with different types of sensed breathing activity.

Figure 8:
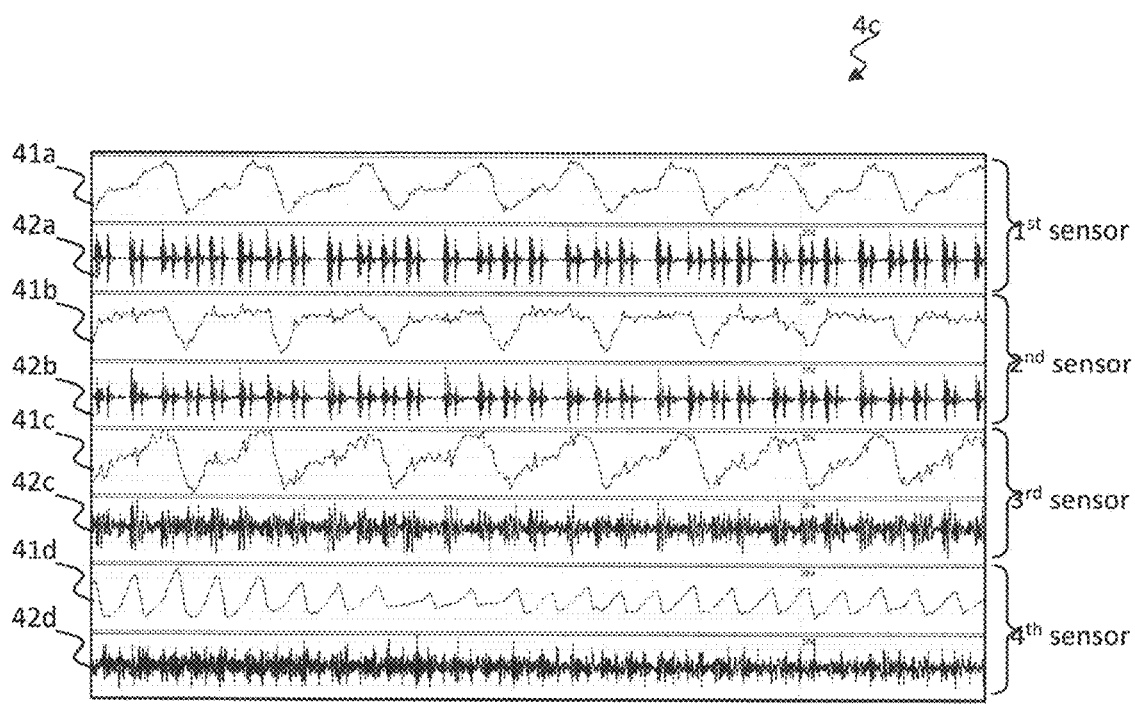
FIG. 8 shows another example of an image produced by the apparatus of FIG. 1.

The signal processing module 21 can determine if a second portion 44 of one or more of the signals is of sufficient quality to be used for diagnostic purposes. For example, it can ascertain a signal amplitude of the second portion and determine that the second portion is of sufficient quality to be used for diagnostic purposes only if the amplitude exceeds a predetermined threshold level. Further, and with reference to the discussions of FIG. 8 below, the signal processing apparatus can identify a part of the second portion of the one or more of the signals corresponding to the subject's heart beat and determine that the second portion is of sufficient quality to be used for diagnostic purposes if the part corresponding to the heart beat has an amplitude that exceeds a predetermined threshold level.

A quality check of the second portion 44 of the signal can be made by the signal processing module 21 by analysis of a segment only of the second portion of the signal. For example, analysis may be performed at the start of the second portion only.

In this embodiment, through identification of the various different portions of the vibration signals, corresponding to changes in body position of the subject and periods of rest, the signal processing module is adapted to carry out an optimisation procedure.

Generally, the use of non-contact sensors means that signal quality across the sensors may vary over a period of time. The subject may move away from any one or more of the sensors when they change their body position, at which point the strength and quality of the vibration signal produced by that vibration sensor is likely to be reduced. However, the subject may nevertheless, at the same time, move towards one or more other of the vibration sensors (or at least move less far away from one or more other of the sensors), such that at least one of the vibration sensors provides a vibration signal of sufficient quality for diagnostic purposes. At any point in time, more than one of the sensors may provide a vibration signal of sufficient quality or only one sensor may provide a signal of sufficient quality. Regardless, when multiple vibration sensors are provided, and thus multiple vibration signals are produced, the highest quality vibration signal can be selected at any point in time and/or for any time period, and subjected to further analysis. By selecting the highest quality vibration signal during different periods of time, an optimised, composite signal can be produced for a particular phase or monitoring.

Figure 5:
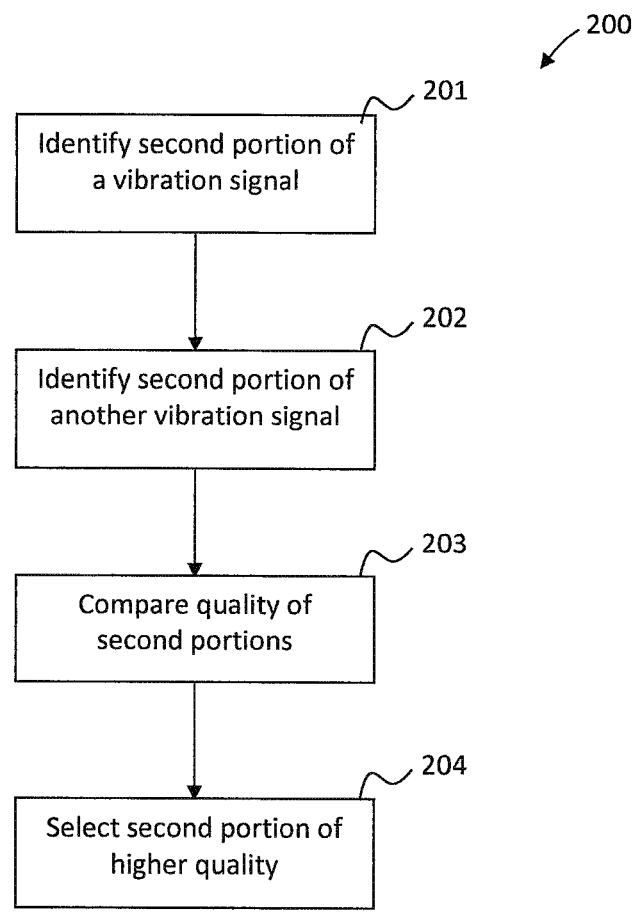
FIG. 5 shows another flowchart that represents steps carried out by processing modules of the apparatus of FIG. 1.

In this embodiment, for the purposes of optimisation, with reference to the flowchart 200 of FIG. 5, at 201 the signal processing module is adapted to identify a second signal portion of one signal, i.e. a portion in which there is substantially no change in body position of the patient. At 202, the signal processing module is adapted to identify a second signal portion of another signal, corresponding to the same time period in which substantially no change in the body position of the patient takes place. At 203, the signal processing module is adapted to compare the quality of the corresponding second portions of the two signals. At 204, the signal processing module is adapted to select the second portion that has the highest signal quality.

Figure 6A:
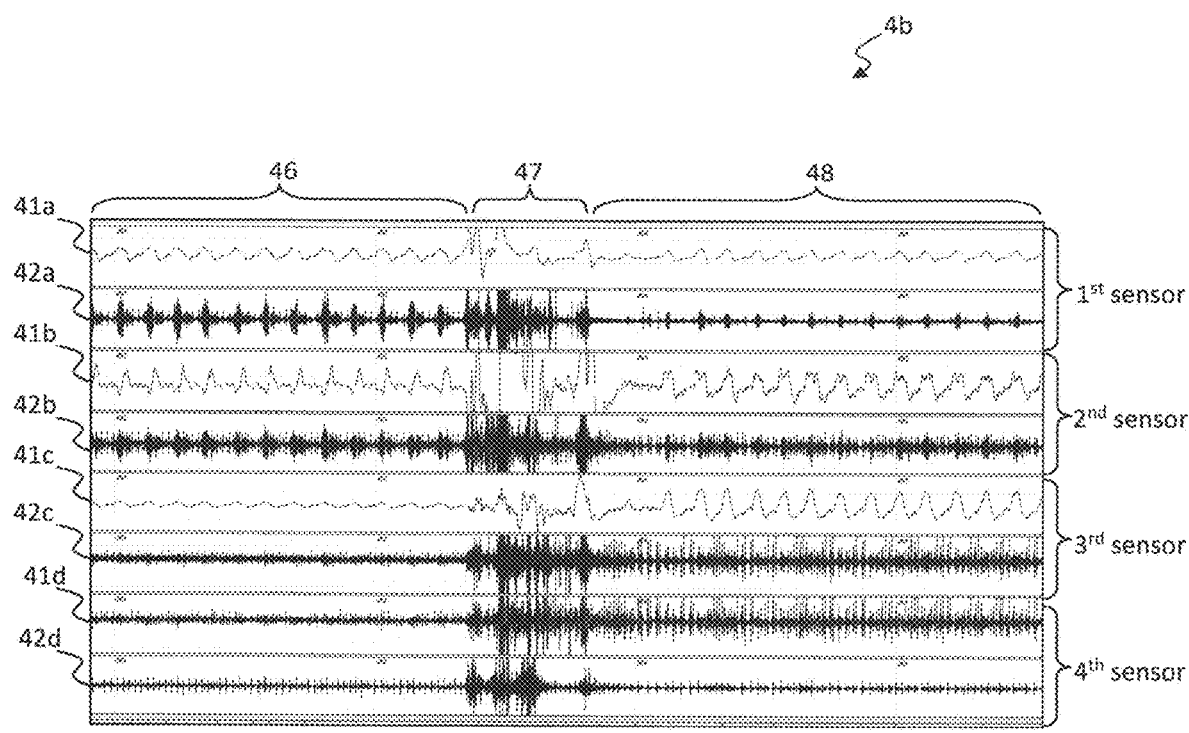

The optimisation process of this embodiment can be further understood with reference to FIG. 6*a*, which shows an image 4*b* in which the effects of changes in body position on signal quality across the vibration sensors 11*a-d* can be seen. A period of time corresponding to a change in body position of the subject is identifiable roughly in the centre of the image 4*b*, indicated by reference number 47. In a period 46 directly before the period of body movement 47, the amplitude of the breathing effort signal 41*c* for the third vibration sensor 11*c* is relatively low. However, in a period 48 directly after the period of body movement 47, the breathing effort signal 41*c* for the third vibration sensor 11*c* has a much higher amplitude and can be considered of better quality.

To the extent that the signal processing module determines, for example, that, prior to the period of body movement 47, the breathing effort signal 41*a* of the first vibration sensor 11*a* has the highest quality of all breathing effort signals 41a-d, and, after the period of body movement 47, the breathing effort signal 41c of the third vibration sensor 11c has the highest quality of all breathing effort signals 41a-d, the signal processing module is adapted to produce an optimised, composite breathing effort signal, as represented in FIG. 4b, in which these two high quality portions signal have been amalgamated. Substantially the same technique can be applied in relation to the breathing flow signals 42a-d to produce an optimised, composite breathing flow signal. Analysis of the subject's breathing effort and/or breathing flow can then be carried out by analysing the optimised, composite signal(s) in some embodiments.

Figure 6B:
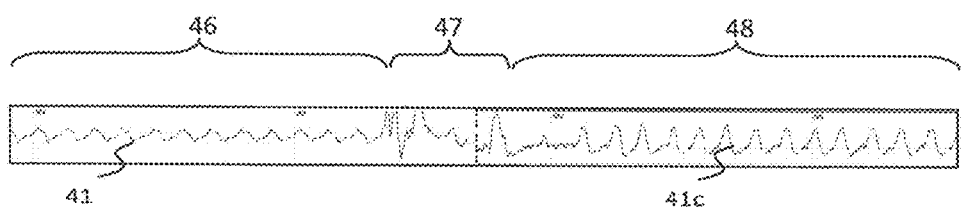
Figure 6C:
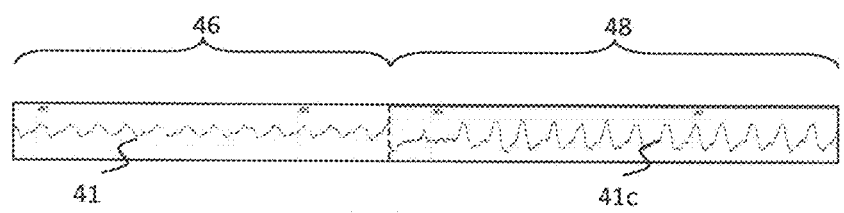

While in FIG. 6b, a signal portion corresponding to the period of body movement 47 has been included in the composite signal, in alternative embodiments it may be excluded, e.g. as represented in FIG. 6c.

While the composite signals may be presented on the display 24, e.g. in a form as represented in FIGS. 6b and 6c, such as to enable analysis of signals by a clinician or other healthcare worker, in some embodiments the composite signal may be produced for internal analysis by the processing apparatus only. When the processing apparatus performs an analysis of the signals for the purposes of diagnosis of a patient over a phase of monitoring, the processing apparatus can perform the analysis with respect to the composite signal.

Through analysis of selected portions of the vibration signals, the apparatus can identify, monitor and/or analyse a variety of different body parameters, behaviours and events, including, but not limited to, breathing, heartbeat, heart function, heart valve abnormalities and murmurs, body reflexes, body positioning, gut activity, teeth grinding and jaw movements, snoring, sleep apnea, sleep state, restriction of airways, asthma, quiescent periods, period spent asleep or awake, fetal heart beat, fetal movements, placental blood flow, crepitation, and/or lung infection, etc. Further, the analysis may identify abnormal body movements and abnormal patterns of movement, which can occur as a result of REM Sleep Movement Disorder, Sleep Myoclonus, and various seizure disorders.

In general, apneic events are characterised by pauses or obstructions in breathing. With reference to FIGS. 7a to 7d, the pauses or obstructions in breathing can be identified through analysis of the breathing effort signal and/or the breathing flow signal.

Figure 7A:
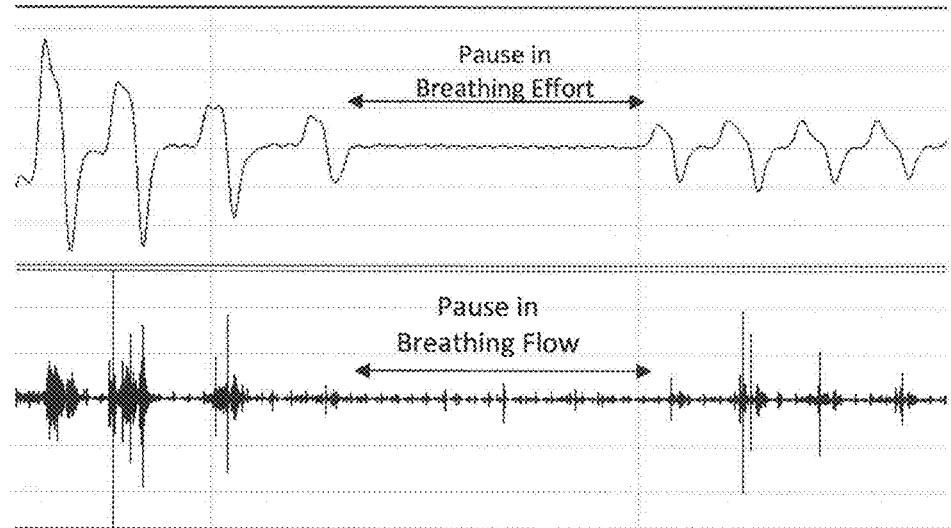
FIGS. 7a to 7d show breathing vibration signal traces which include pauses, obstructions and/or reductions in amplitude indicative of central apnea, obstructive apnea, mixed apnea and hypopnea.

Central apnea occurs when no direction to breathe is transmitted from the brain. Referring to FIG. 7a, central apnea is therefore determined in this embodiment through identification of a pause in both the breathing effort signal and the breathing flow signal. The pause is identified as a period in which the signal level does not rise above background noise for a period of time exceeding a predetermined threshold period of time, the pause being immediately preceded and followed by periods in which the signal level does rise above background noise. In alternative embodiments, a pause can be identified as a period in which the signal level has a reduction in amplitude, e.g., of at least 90%, in comparison to preceding and/or subsequent periods, for a period of time exceeding a threshold period of time. The threshold period of time in this embodiment is 10 seconds for adults, although a variety of different threshold levels may be selected.

Figure 7B:
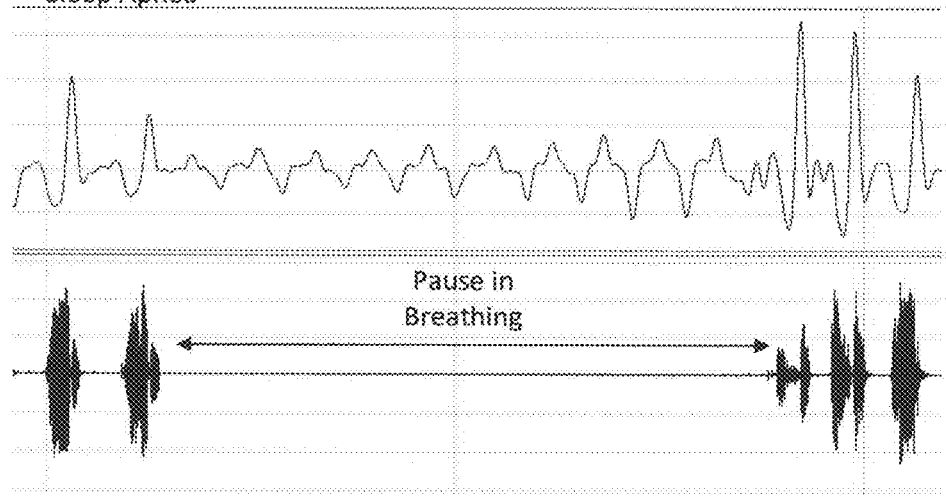

Obstructive sleep apnea occurs upon obstruction of the upper airway, e.g. when relaxation causes the palate and tongue to close the upper airway (throat). Referring to FIG. 7b, obstructive apnea is therefore determined in this embodiment through identification of a pause in the breathing flow signal but not the breathing effort signal. The pause is identified in a manner discussed above with respect to FIG. 7a.

Figure 7C:
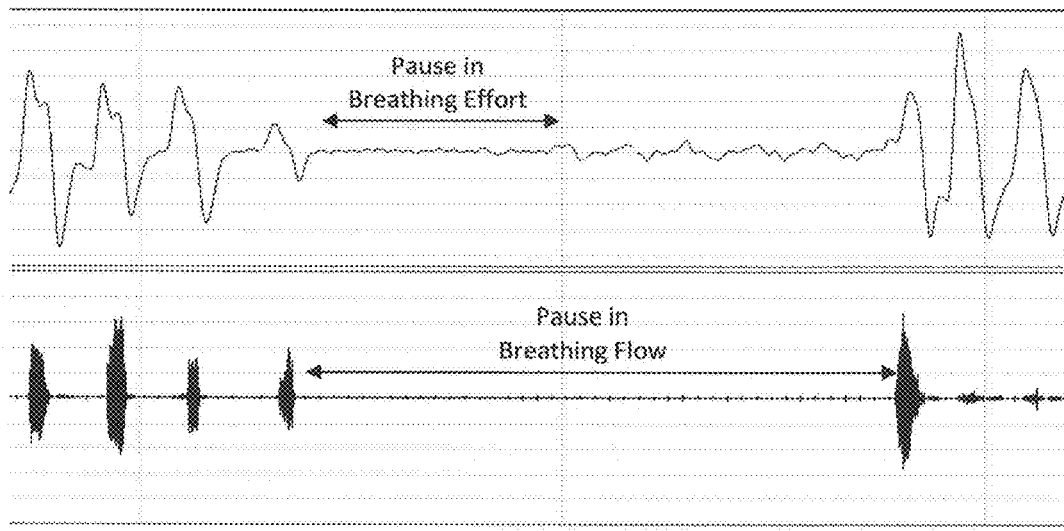

Mixed apnea occurs when, over a predetermined analysis period, both central apnea and obstructive apnea can be identified. With reference to FIG. 7c, mixed apnea is therefore determined in this embodiment through identification of one or more periods in which there is a pause in both the breathing effort signal and the breathing flow signal, and identification of one or more periods in which there is a pause in the breathing flow signal but not the breathing effort signal.

Figure 7D:
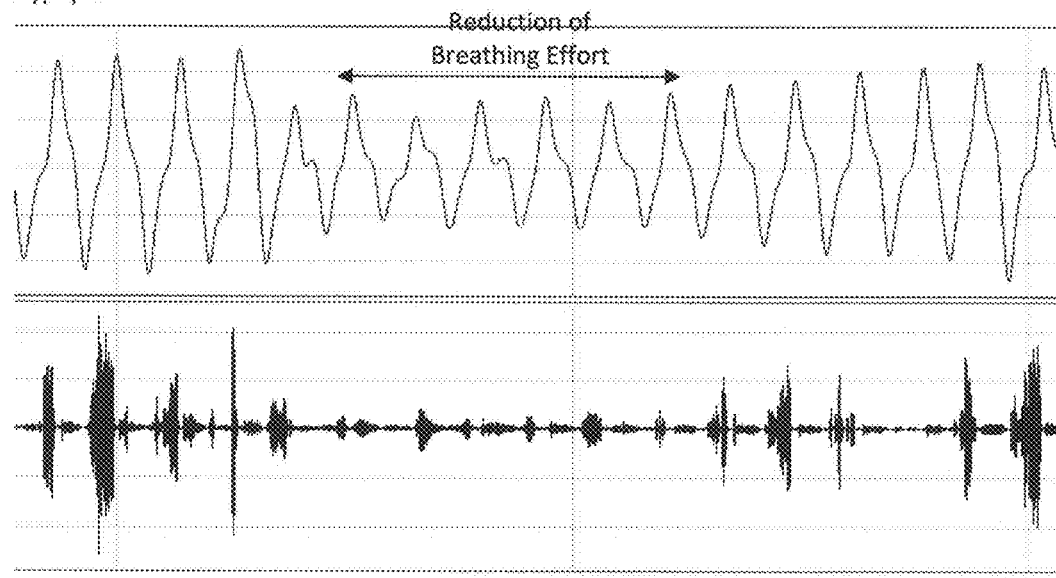

Central Hypopnea occurs when there is a change (e.g., reduction) of breathing effort, over a period of time coupled with a change (e.g., reduction) of breath sound intensity. With reference to FIG. 7d, hypopnea is determined in this embodiment through identification of one or more periods in which breathing effort amplitude falls below a predetermined threshold level.

As indicated above, analysis of selected portions of the vibration signals can also allow information about fetal behaviour to be determined. This can be further understood with reference to FIG. 8, which shows an image 4c in which a second portion of signals produced from the four vibration sensors 11a-d can be seen. The higher frequency output 42d from the fourth sensor 11d is indicative of the fetal heartbeat. On the other hand the outputs from the first to third sensors 11a-c are indicative of the breathing and heart sound related signals of the mother.

In one embodiment, the apparatus discussed above with reference to FIGS. 1 and 2 is adapted to estimate duration of a period of sleep of a subject. Again, the signal processing module is adapted to identify first, second and third portions of at least one of the vibration signals, but in this embodiment it is further adapted to identify one or more respiratory indicators of sleep in the second portion of the vibration signal and estimate sleep onset time of the subject as the earlier of: (i) a predetermined threshold time (x), if the second period of time extends after the end of the first period of time for a time that is equal to or greater than the predetermined threshold time (x): or (ii) a time at which the earliest respiratory indicator of sleep in the second portion of the vibrations signal (such as a snore or breath sound change) is identified. The apparatus is adapted to calculate a duration of a period of sleep of the subject as the time between the estimated sleep onset time and the start of the third time period.

Figure 9:
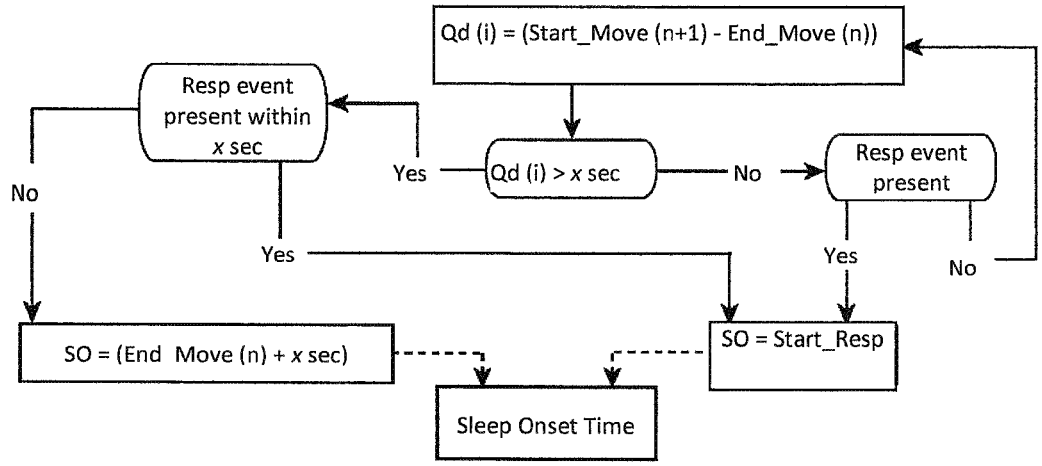
FIG. 9 shows a flow chart illustrating how sleep onsite time can be estimated by a signal processing module of the apparatus of FIG. 1.

FIG. 9 provides a flow chart illustrating how sleep onset time is estimated by the signal processing module in this embodiment. Starting at the top most rectangle, if periods of immobility (Qd) are not longer than a constant value (x sec) and there are no respiratory indicators of sleep, the analysis continues until either a respiratory indicator of sleep occurs or a Qd period exceeds x sec. The dotted arrows indicate that a sleep onset time has been identified and recorded. Once sleep onset has been identified the duration of time between it and the beginning of the next body movement is considered to be sleep time, (In FIG. 9: Qd (i)=Initial Qd; SO=sleep onset; x=Qd time threshold (sec); Start_Move=start time of body movement; End_Move=end time of body movement and Start_Resp=start time of respiratory event.)

Figure 10:
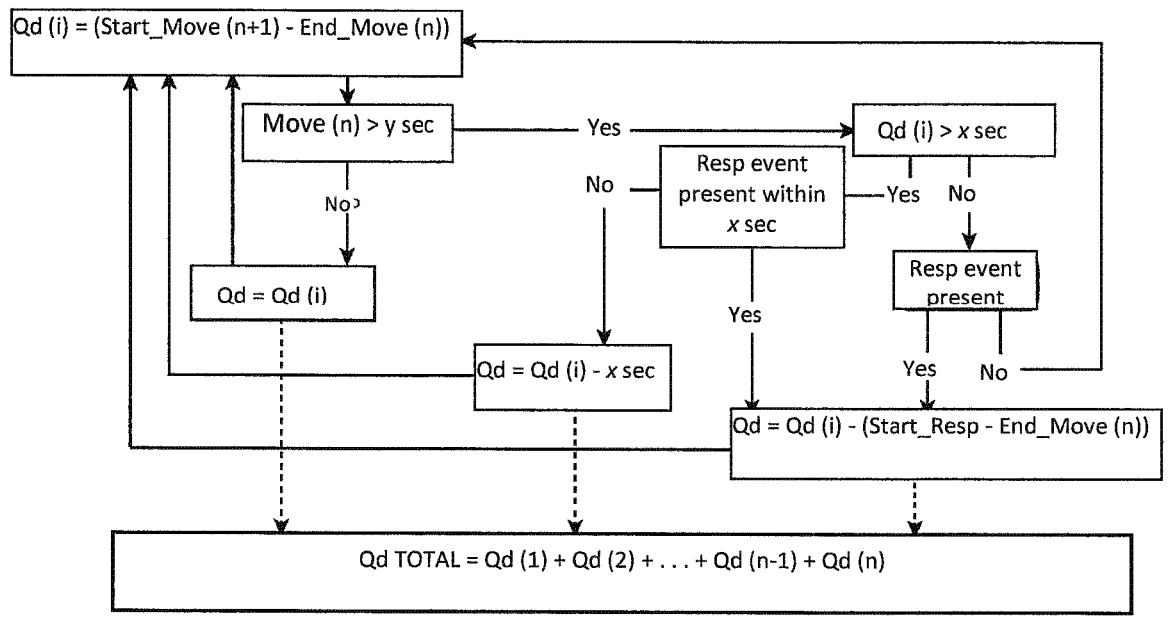
FIG. 10 shows a flow chart illustrating how durations of sleep periods can be estimated by the signal processing module of the apparatus of FIG. 1.

FIG. 10 provides a flow chart illustrating how durations of sleep periods are estimated by the signal processing module. Once sleep onset has been identified in accordance with the approach discussed above with respect to FIG. 9, all subsequent body movements and Qd periods are analysed for the entire study starting at the top most rectangle. A subject is considered to stay asleep until a movement in excess of a constant duration (y sec) occurs. Following this, the subject returns to sleep only if the Qd is >x seconds or a respiratory indicator of sleep occurs. The dotted arrows indicate that a period of quiescent time is collated for the calculation of a QdTOTAL, the total sleep time. (In FIG. 10: Qd=Quiescent time; Qd (i)=Initial Qd; SO=sleep onset; x=Qd time threshold (sec); y=body movement threshold (sec); Start_Move=start time of body movement; End_Move=end time of body movement; and Start_Resp=start time of respiratory event).

This approach enables Qd periods that are associated with a high probability of sleep to be identified and accounts for subjects both waking from sleep and for short periods of quiescence that occur in the presence of respiratory events. Each period of Qd is sequentially identified and either does not meet the criteria for sleep and is discarded or does meet the criteria and is included in a total sleep time (TST) value. If there are any body movements >y seconds, it is assumed that the period following this body movement has reverted to the wake state and the subject must now lie immobile for >x seconds or a respiratory indicator of sleep must be present before it can be assumed that sleep has once again occurred.

Method

Signal recordings, in particular polysomnographic (PSG) recordings from 30 adult subjects were obtained and results compared data generated from EEG recordings in this same group of subjects. The PSG studies Were recorded from patients referred for investigation of possible sleep-disordered breathing.

In accordance with FIGS. 9 and 10 and the discussions above, variables x and y were to be determined and in order to ascertain these values, two non-standard events were scored in each PSG study.

The first non-standard event was labeled "Sleep Onset" (SO) and was scored at the precise point in time that the EEG indicated that sleep had occurred. The time elapsed between the beginning of a SO event to the beginning of an EEG arousal was considered to be sleep time and the time elapsed between the beginning of an EEG arousal to the be of the subsequent SO event was considered to be wake time. These absolute measures allowed the identification of blocks (or runs) of sleep and wake to be identified.

The second non-standard event was called "Body movement" (BM) and was identified on thoracic and/or abdominal traces of the PSG study as an abrupt change in the normal pattern of respiration identical to the patterns shown for body movement detection.

A threshold of 3 seconds was selected as the minimum duration of a BM event as it was equivalent to the minimum length of a determined EEG arousal.

The duration of each BM event and the duration of the periods of quiescence between each BM event were calculated.

Runs of absolute wake (EEG arousal to SO event) and absolute sleep (SO event to EEG arousal) of adequate duration (>1 minute) were identified. Within these discrete periods of time, and multiple periods were present for each subject, the BM events and periods of Qd were analysed.

Variables x and y were obtained from the durations of Qd that occurred during wake and the durations of body movements that occurred during sleep.

Figure 11:
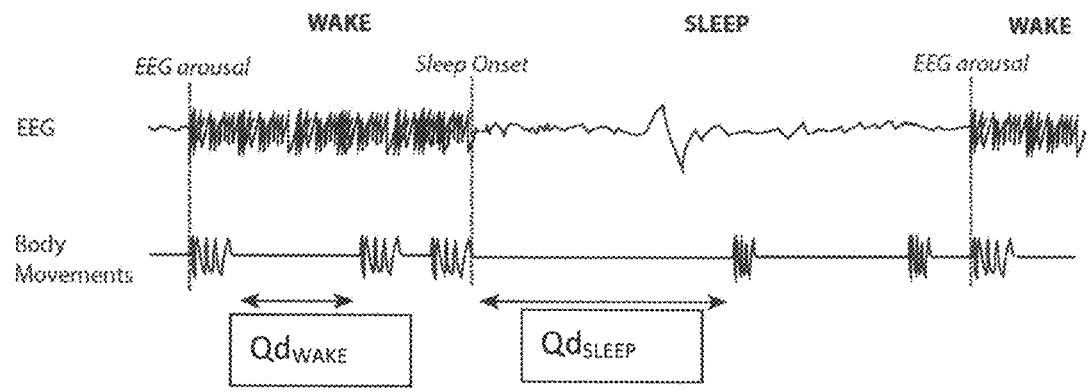
FIG. 11 shows vibration signal traces illustrating quiescent periods and body movements in runs of wake and sleep.

FIG. 11 provides an illustration of Qd and body movements in runs of wake and sleep. The top trace indicates the EEG state and the bottom trace indicates body movements present on the thoracoabdominal PSG traces. Periods of quiescence are represented as straight horizontal lines between body movements (breathing movements are present on the actual PSG recordings but not represented in the illustration). Wake occurs between an EEG arousal and a Sleep Onset event and sleep occurs between a Sleep Onset event and an EEG arousal. Vertical dotted lines indicate the boundaries of runs of sleep and wake and the duration of these runs varied. Within each run of sleep and wake the duration of all body movement (≥3 seconds) and quiescence (QdWAKE and QdSLEEP) were collated.

Once the data was collated, the 95th centile values of each measure (movement duration and Qd duration) were used in the processes described above with reference to FIGS. 9 and 10, to estimate the TST. The TST generated from epoch scoring and that generated from the absolute scoring of the EEG were both compared to the experimental results in order to examine accuracy.

Results

Thirty PSG studies were analysed (15 male, age=58±12 years, BMI=29.5±5.4 kg/m2). In these studies there were 133 runs of wake and 239 runs of sleep >60 seconds. Within these periods 1,260 body movements occurred during wake and 349 body movements occurred during sleep. There were 1,121 periods of quiescence during wake and 570 periods of quiescence during sleep. There was a significant difference between the duration of movements (MoveWAKE=11.0 (7.0, 22.0) and MoveSLEEP=7.0 (4.0, 10.0) seconds; p<0.0001) and the quiescent time (QdWAKE=17.0 (8.0, 37.0) and $Qd_{SLEEP}$=98.0 (32.0, 297.3) seconds; p<0.0001) that occurred during wake and sleep.

Table 1 below lists the percentile values of quiescent times and body movement durations during runs of wake and runs of sleep. The 95th centile for quiescent time during wake was 110 seconds, indicating that only 5% of all periods of quiescence during EEG defined wake were longer than this. The 95th centile for body movements during sleep was 16 seconds, indicating that only 5% of body movements that occur during EEG defined sleep were longer than this. These two constants were used for values x and y, respectively.

TABLE 1

| Centiles | MoveWAKE | MoveSLEEP | QdWAKE | QdSLEEP |
| --- | --- | --- | --- | --- |
| 5th | 4.0 | 3.0 | 3.0 | 8.0 |
| 25th | 7.0 | 4.0 | 8.0 | 32.0 |
| 50th | 11.0 | 7.0 | 17.0 | 98.0 |
| 75th | 22.0 | 16.0 | 37.0 | 295.8 |
| 95th | 65.0 | 16.0 | 110.0 | 928.4 |

Figure 12:
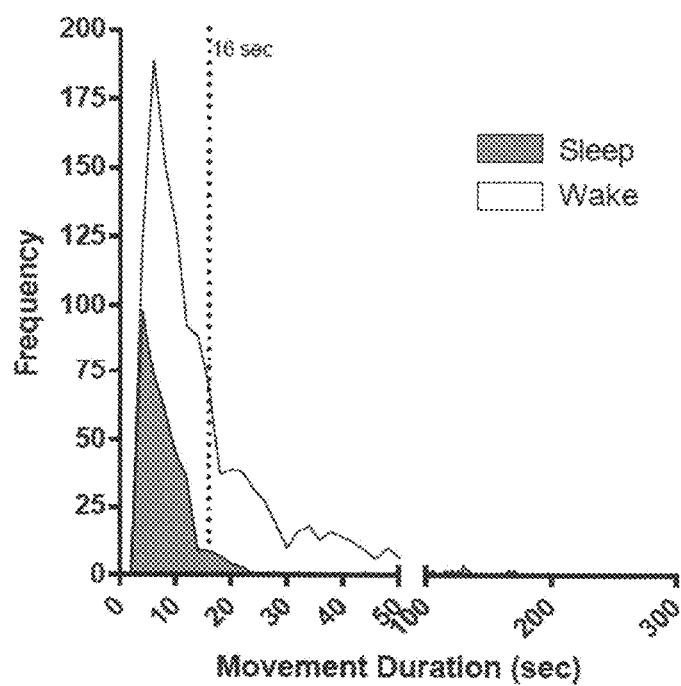
FIG. 12 shows a frequency distribution of body movements in wake and sleep within PSG recordings recorded in an example of the present disclosure.

The frequency distribution of body movements in wake and sleep within the PSG recordings is presented in FIG. 12, The 95th centile for body movements that occurred during sleep (16 seconds) is shown as the vertical marker. Both wake and sleep are associated with considerable numbers of brief body movements <16 seconds and, although there are movements >16 seconds that occur during sleep, they are very few compared to the number that occur during wake. There is a long tail of movement durations that occur during wake.

Figure 13:
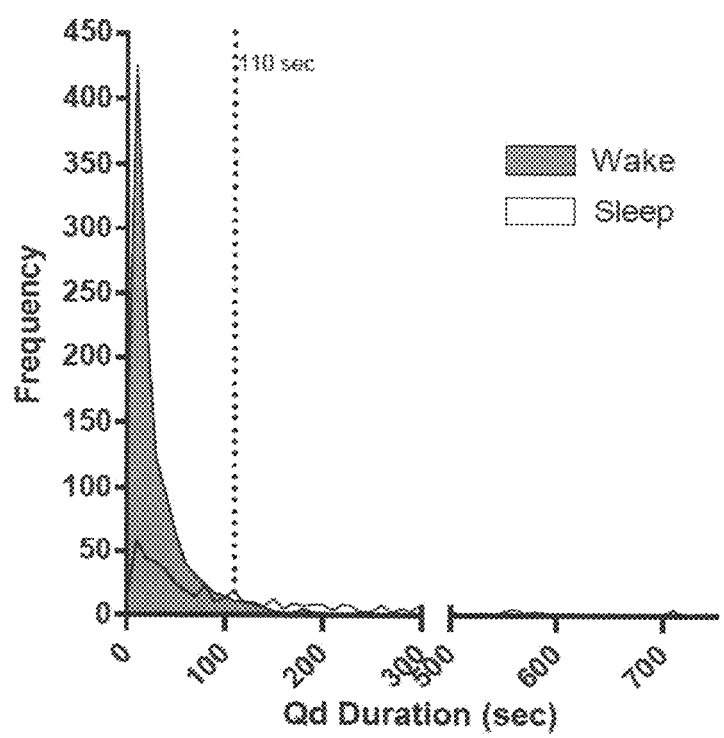
FIG. 13 shows a frequency distribution of quiescent periods in wake and sleep within the PSG recordings recorded in the example of the present disclosure.

The frequency distribution of quiescent periods in wake and sleep within the PSG recordings is presented in FIG. 13. The 95th centile for the quiescent time duration that occurred during wake (110 seconds) is shown as the vertical marker. Both wake and sleep are associated with considerable numbers of quiescent periods <110 seconds but there are very few quiescent periods >110 seconds that occur during wake. In contrast there is a very long tail of quiescent durations above this threshold that occur during sleep.

In summary, from the data gathered using PSG studies, if a subject did not move for >110 seconds there was only a 5% chance that that the subject remained awake. In addition, once the subject was asleep, if a subject moved for >16 seconds there was only a 5% chance that they remained asleep following the movement. Based on this, once a subject lies down with the intention to sleep they must be immobile for >110 seconds to be considered asleep. It is beyond this sleep onset point that the calculation of TST begins.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A system comprising:
at least first and second sensors positioned in or on a support, the support being adapted to receive a subject, the first sensor being adapted to produce a first signal indicative of movement of the subject over time and the second sensor being adapted to produce a second signal indicative of movement of the subject over time;
a display; and
processing apparatus configured to:
receive the first and second signals and, for each of the first and second signals:
identify a first portion of that signal that corresponds to a first time period during which the subject is determined to have changed body position on the support,
identify a third portion of that signal that corresponds to a third time period during which the subject is determined to have changed body position on the support,
identify a second portion of that signal that corresponds to a second time period, between the first and third time periods, during which no change in body position of the subject on the support is determined to have taken place,
identify a heartbeat signal in the second portion of that signal based on a first frequency and a first amplitude of that signal, the heartbeat signal being a heartbeat component of that signal indicative of the subject's heartbeat,
identify a breathing signal in the second portion of that signal based on a second frequency and a second amplitude of that signal, the breathing signal being a breathing component of that signal indicative of the subject's breathing, and
determine a sufficiency quality of the breathing signal based on the first amplitude of the heartbeat signal;
determine a breathing signal having a higher sufficiency quality from among the breathing components of the first signal and the second signal, wherein higher sufficiency quality is determined based on a higher amplitude between the first amplitude of the first signal and the first amplitude of the second signal; and
select the first or second signal corresponding to the determined breathing signal having the higher sufficiency quality for display on the display.

2. The system of claim 1, wherein the first and second sensors are vibration sensors and the first signal and the second signal are indicative of vibrations caused by the subject over time.

3. The system of claim 1, wherein the support comprises a mat or mattress and the first and second sensors are embedded in the mat or mattress.

4. The system of claim 1, wherein the processing apparatus is configured to evaluate a segment at the start of the second portion of the at least one of the first and second signals to determine the sufficiency quality.

5. The system according to claim 1, wherein the processing apparatus being configured to:
identify one or more respiratory indicators of sleep in the selected signal and estimate sleep onset time of the subject as the earlier of:
(i) a predetermined threshold time (x), if the second period of time extends after an end of the first period of time for a time that is equal to or greater than the predetermined threshold time (x), or
(ii) a time at which the earliest respiratory indicator of sleep in the selected signal is identified; and
calculate a duration of a period of sleep of the subject as the time between the estimated sleep onset time and a start of the third time period.

6. The system of claim 5, wherein no change in body position of the subject is determined to have taken place if any body movement that is identifiable lasts less than a body movement threshold time (y).

7. The system of claim 1, wherein the subject is not tethered to any of the at least first and second sensors.

8. The system of claim 1, wherein the subject is a mobile ambulatory subject that is free to move relative to the at least first and second sensors and support.

9. The system of claim 1, wherein a plurality of sensors including the at least first and second sensors are provided in an array formation in or on the support to form a sensor field.

10. The system of claim 1, wherein the breathing signal comprises a breathing flow signal.

11. The system of claim 1, wherein the breathing signal comprises a breathing effort signal.

12. The system of claim 1, wherein the breathing signal comprises a breathing flow signal and a breathing effort signal.

13. A method of receiving signals indicative of physiological activity, the method comprising:
receiving a first signal from a first sensor positioned in or on a support adapted to receive a subject and a second signal from a second sensor positioned in or on the support, wherein each of the first and second signals is indicative of movement of the subject over time, and for each of the first and second signals:
identifying a first portion of that signal that corresponds to a first time period during which the subject is determined to have changed body position on the support,
identifying a third portion of that signal that corresponds to a third time period during which the subject is determined to have changed body position on the support,
identifying a second portion of that signal, that corresponds to a second time period, between the first and third time periods, during which no change in body position of the subject on the support is determined to have taken place, identifying a heartbeat signal in the second portion of that signal, the heartbeat signal being a heartbeat component of that signal indicative of the subject's heartbeat based on a first frequency and a first amplitude of that signal, identifying a breathing signal in the second portion of that signal, the breathing signal being a breathing component of that signal indicative of the subject's breathing based on a second frequency and a second amplitude of that signal, and determining a sufficiency quality of the breathing signal for diagnostic purposes based on the first amplitude of the heartbeat signal, determining a breathing signal having a higher sufficiency quality from among the breathing components of the first signal and the second signal, wherein higher sufficiency quality is determined based on a higher amplitude between the first amplitude of the first signal and the first amplitude of the second signal; and selecting the first or second signal corresponding to the determined breathing signal having the higher sufficiency quality for displaying.

14. A non-transitory machine readable medium comprising instructions stored therein, which when executed by a processor, causes the processor to perform operations comprising:

receiving a first signal produced by a first sensor positioned in or on a support adapted to receive a subject and receiving a second signal produced by a second sensor positioned in or on the support, wherein the first signal and the second signal are indicative of movement of the subject over time, for each of the first signal and the second signal:
identifying a first portion of that signal that corresponds to a first time period during which the subject is determined to have changed body position on the support, identifying a third portion of that signal that corresponds to a third time period during which the subject is determined to have body position on the support, identifying a second portion of that signal that corresponds to a second time period, between the first and third time periods, during which no change in body position of the subject on the support is determined to have taken place, identifying a heartbeat signal in the second portion of that signal based on a first frequency and a first amplitude of that signal, the heartbeat signal being a heartbeat component of that signal indicative of the subject's heartbeat, identifying a breathing signal in the second portion of that signal based on a second frequency and a second amplitude of that signal, the breathing signal being a breathing component of that signal indicative of the subject's breathing, and determining a sufficiency quality of the breathing signal based on the first amplitude of the heartbeat signal, determining a breathing signal having a higher sufficiency quality from among the breathing components of the first signal and the second signal, wherein higher sufficiency quality is determined based on higher amplitude between the first amplitude of the first signal and the first amplitude of the second signal; and selecting the first or second signal corresponding to the determined breathing signal having the higher sufficiency quality for displaying.

15. A processor configured to:

receive a first signal produced by a first sensor positioned in or on a support adapted to receive a subject and receive a second signal produced by a second sensor positioned in or on the support, wherein the first signal and the second signal are indicative of movement of the subject over time;

for each of the first and second signals:
identify a first portion of that signal that corresponds to a first time period during which the subject is determined to have changed body position on the support, identify a third portion of that signal that corresponds to a third time period during which the subject is determined to have changed body position on the support, identify a second portion of that signal that corresponds to a second time period, between the first and third time periods, during which no change in body position of the subject on the support is determined to have taken place, identify a heartbeat signal in the second portion of that signal based on a first frequency and a first amplitude of that signal, the heartbeat signal being a heartbeat component of that signal indicative of the subject's heartbeat, identify a breathing signal in the second portion of that signal based on a second frequency and a second amplitude of that signal, the breathing signal being a breathing component of that signal indicative of the subject's breathing, and determine a sufficiency quality of the breathing signal based on the first amplitude of the heartbeat signal;

determine a breathing signal having a higher sufficiency quality from among the breathing components of the first signal and the second signal, wherein higher sufficiency quality is determined based on higher amplitude between the first amplitude of the first signal and the first amplitude of the second signal; and select the first or second signal corresponding to the determined breathing signal having the higher sufficiency quality for display.

\* \* \* \* \*